(12) United States Patent
Alameri et al.

(10) Patent No.: US 9,598,732 B2
(45) Date of Patent: Mar. 21, 2017

(54) METHOD OF IDENTIFYING DATE PALM GENDER USING SCAR PRIMERS

(71) Applicant: KING SAUD UNIVERSITY, Riyadh (SA)

(72) Inventors: Abdulhafed Abdullah Hassan Alameri, Riyadh (SA); Fahad Hamad Al-Qurainy, Riyadh (SA); Salim Khan, Riyadh (SA); Mohammad Nadeem, Riyadh (SA); Abdel-Rhman Zakaria Gaafar, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/960,666

(22) Filed: Dec. 7, 2015

(65) Prior Publication Data
US 2016/0273039 A1    Sep. 22, 2016

Related U.S. Application Data

(63) Continuation of application No. 14/663,403, filed on Mar. 19, 2015.

(51) Int. Cl.
C12Q 1/68      (2006.01)

(52) U.S. Cl.
CPC ......... *C12Q 1/6879* (2013.01); *C12Q 1/6806* (2013.01); *C12Q 1/6895* (2013.01); *C12Q 2600/13* (2013.01)

(58) Field of Classification Search
None
See application file for complete search history.

Primary Examiner — David Thomas
(74) Attorney, Agent, or Firm — Richard C. Litman

(57) ABSTRACT

The method of identifying Date Palm gender using SCAR primers includes using modern genetics techniques for detecting a novel sex-linked marker (SEQ ID NO: 1) in a Date Palm sample. The presence of the Date Palm sex-linked marker (SEQ ID NO: 1) in the sample is indicative that the sample is from a male Date Palm plant. The method of identifying Date Palm gender to determine the gender of Date Palms can be used to determine the gender of Date Palms of any age.

13 Claims, 2 Drawing Sheets

SEQUENCE LISTING

<160> NUMBER OF SEQ ID NOS: 4

<210> SEQ ID NO 1
<211> LENGTH: 294
<212> TYPE: DNA
<213> ORGANISM: Phoenix dactylifera

<400> SEQUENCE: 1

```
gaacggactc tgaaatgtag gggatttggc tgagatgagg acgcgtgaaa cagggatgt      60 ttggatgccg tgaaactcac aagaatggag ctgatccgtg ggatgaggta gtttgggatg     120
ttgggaagag gtgatttcga aacagggaa gtggatgaag atagatcaac gtggatgtga      180
ttccgaggga ggctgggttg gttcggaaga gggaagacac tggatttggt taggatgaaa     240
tctaggaaga tgctgggaag attggttggt ttgcatcgcg agaggagtcc gttc           294
```

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

```
cgtgggatga ggtagtttgg                                                  20
```

```
<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
ctcgcgatgc aaaccaacca a                                             21

<210> SEQ ID NO 4
<211> LENGTH: 10
<212> TYPE: DNA
<213> ORGANISM: Artificial Sequence
<220> FEATURE:
<223> OTHER INFORMATION: Primer

<400> SEQUENCE: 4
gaacggactc                                                          10
```

METHOD OF IDENTIFYING DATE PALM GENDER USING SCAR PRIMERS

CROSS-REFERENCE TO RELATED APPLICATIONS

This is a continuation of the prior application Ser. No. 14/663,403, filed Mar. 19, 2015, now pending.

INCORPORATION BY REFERENCE OF MATERIAL SUBMITTED IN COMPUTER READABLE FORM

The Applicants hereby incorporate by reference the sequence listing contained in the ASCII text file titled 32693_12_sequence_listing_ST25.txt, created Mar. 10, 2015 and having 1.07 KB of data.

BACKGROUND OF THE INVENTION

1. Field of the Invention

The present invention relates to early identification of the gender of individual plants of the species *Phoenix dactylifera* ("Date Palm"), and particularly to identifying Date Palm gender using Sequence Characterized Amplified Regions ("SCAR") primers specific for a novel sex-linked genetic sequence.

2. Description of the Related Art

The Date Palm is a long-lived dioecious monocotyledon, which is cultivated in arid regions for food, fiber, and shelter. It is a member of the Palmae family and its fruit, dates, are known to provide a good source of energy, vitamins, phosphorus, iron, zinc, selenium, manganese, and calcium. (Ellecuh, M. et al., "Date flesh: chemical composition and characteristics of the dietary fiber," Food Chem. 111: 67-82 (2008)) Because of these characteristics, the Date Palm is an economically important crop in arid zones, including many Middle-Eastern Countries.

Unfortunately, the gender of individual Date Palm plants cannot be determined until they reach reproductive age, between five and ten years old. This significantly increases the cost of cultivating Dates from seeds, as only the female plants bear fruit. A reliable method of early detection of Date Palm gender would significantly increase the profits of seed based cultivation.

Historically, this issue has been addressed by propagating Date Palm cultivars through offshoots. However, reliance upon offshoot propagation reduces genetic diversity, increasing the risk of catastrophic loss to diseases and decreasing the capacity of the plants to survive changes in environmental conditions. Thus, a method of identifying Date Palm gender using a reliable genetic marker such as a sex-linked SCAR marker is desired.

SUMMARY OF THE INVENTION

The method of identifying Date Palm gender using SCAR primers includes detecting the presence or absence of a novel sex-linked marker (SEQ ID NO: 1) in a Date Palm sample. The sex-linked marker (SEQ ID NO: 1) is exclusively found in male Date Palm plants. The method of identifying Date Palm gender using SCAR primers includes obtaining a sample of a Date Palm plant and determining a presence or absence of the Date Palm sex-linked marker (SEQ ID NO: 1) in the sample. The presence of the Date Palm sex-linked marker (SEQ ID NO: 1) in the sample is indicative that the sample is from a male Date Palm plant. Using the sex determination method for a Date Palm plant, the sex of Date Palm plants may be determined prior to flowering of the Date Palm plants.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The method of identifying date palm gender using SCAR primers may include obtaining a sample of a Date Palm plant and determining a presence or absence of the Date Palm sex-linked marker (SEQ ID NO: 1) in the sample. The presence of the Date Palm sex-linked marker (SEQ ID NO: 1) in the sample is indicative that the sample is from a male Date Palm plant. The sample may be obtained from any part of the Date Palm plant at any stage of development of the Date Palm plant. For example, the sample may include but is not limited to plant tissue (including leaves, seeds, petals, flowers, bark, etc.), extracts of plant tissue, and/or plant body fluid. Thus, using the sex determination method for a Date Palm plant, the sex of Date Palm plants may even be determined when the Date Palm plants are still young, i.e., prior to flowering of the plants. The method of identifying date palm gender using SCAR primers allows farmers to combine the genetic diversity benefits of growing dates from seeds with the economic benefits of screening out male plants prior to planting their fields.

Figure 1:
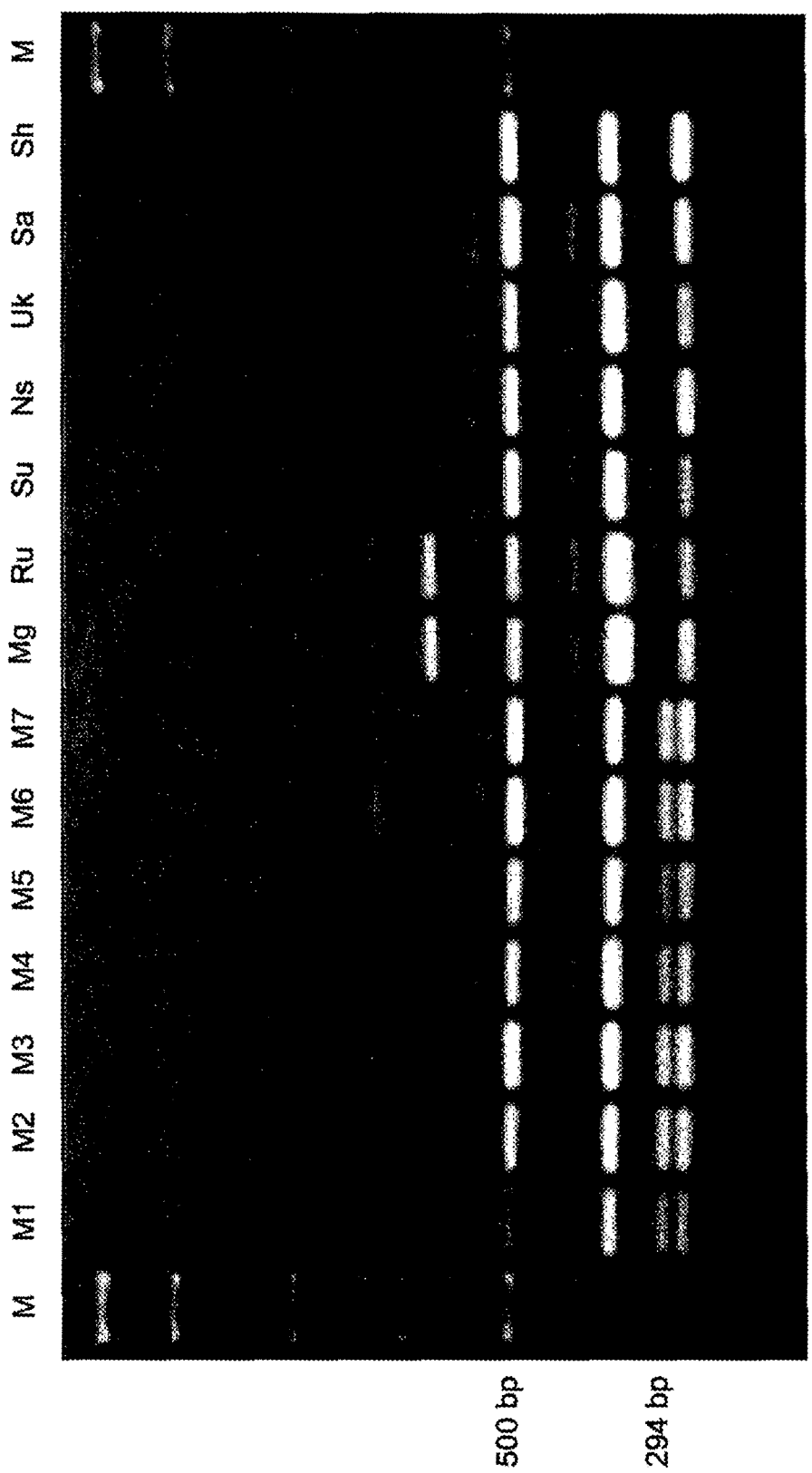
FIG. 1 is a view of the results of gel electrophoresis performed on the products amplified by RAPD primer (SEQ ID NO: 4), demonstrating the presence of a 294 base pair band used to develop SCAR primers (SEQ ID NO: 2 and SEQ ID NO 3) according to the present invention.

The sex-linked marker was identified using RAPD primers. RAPD primers are short nucleotide sequences (generally 8-12 base pairs long). The inventors screened 300 RAPD primers to identify a sex-linked marker in Date Palms. For example, the gel pictured in FIG. 1 illustrates the results of a PCR reaction using one such RAPD primer (SEQ ID NO: 4). In FIG. 1 (M) is a 100 base pair marker, (M1-M7) are male Date Palm samples, and (Ru-Sh) are female Date Palm samples. The 294 base pair band present exclusively in the lanes corresponding to the male Date Palm samples was cut out, isolated, and sequenced, revealing the sex-linked marker (SEQ ID NO: 1). This sequence was then used to develop SCAR primers specific to the sex-linked marker, called ALAMERI-F (SEQ ID NO: 2) and ALAMERI-R (SEQ ID: 3).

Based on the discovery of the present inventors, the sex of a Date Palm plant may be genetically determined by determining a presence or absence of the Date Palm sex-linked marker (SEQ ID NO: 1) in a Date Palm plant sample. Determining a presence or absence of the Date Palm sex-linked marker (SEQ ID NO: 1) in the Date Palm plant sample may be carried out by any method known in the art. For example, determining a presence or absence of the Date Palm sex-linked marker (SEQ ID NO: 1) in the Date Palm plant sample may include extracting nucleic acids from the sample, contacting under amplification conditions the nucleic acid from the sample with a Date Palm sex-linked marker specific primer pair, and detecting the presence or absence of amplification products or amplicons. The presence of amplification products may indicate the presence of the male-specific sex-linked marker in the Date Palm plant, i.e., that the sample is from a male plant. The absence of amplification products may indicate that the sample is from a female plant.

Alternatively, the presence or absence of the Date Palm sex-linked marker (SEQ ID NO: 1) in the sample may be determined by detecting a protein encoded by the Date Palm plant sex-linked marker (SEQ ID NO: 1) in the Date Palm plant sample using, for example, an enzyme-linked immunosorbent assay (ELISA).

As discussed above, the nucleic acid extracted from the sample may be subjected to amplification conditions using male-specific sex-linked marker primer pairs. The male-specific sex-linked marker primer pairs may include primers specific for amplification of the Date Palm sex-linked marker (SEQ ID NO: 1). Individual primers may correspond to any 15-30 base pair region of the Date Palm sex-linked marker (SEQ ID NO: 1) or its complement. For example, the male-specific sex-linked marker primer pairs may include an oligonucleotide primer including SEQ ID NO: 2 and an oligonucleotide primer including SEQ ID NO: 3. The male-specific sex-linked marker primer pairs may include other primers specific for amplification of the Date Palm Sex-linked marker (SEQ ID NO: 1). The presence of any amplification products may indicate the presence of a male-specific sex-linked marker in the Date Palm plant, i.e., that the Date Palm plant sample is from a male Date Palm plant. The presence of amplification products of a particular size may be further indicative of the presence of a male-specific sex-linked marker in the Date Palm plant. For example, amplification products having a size of approximately 186 base pairs may indicate that the Date Palm plant sample is from a male Date Palm plant.

Figure 2:
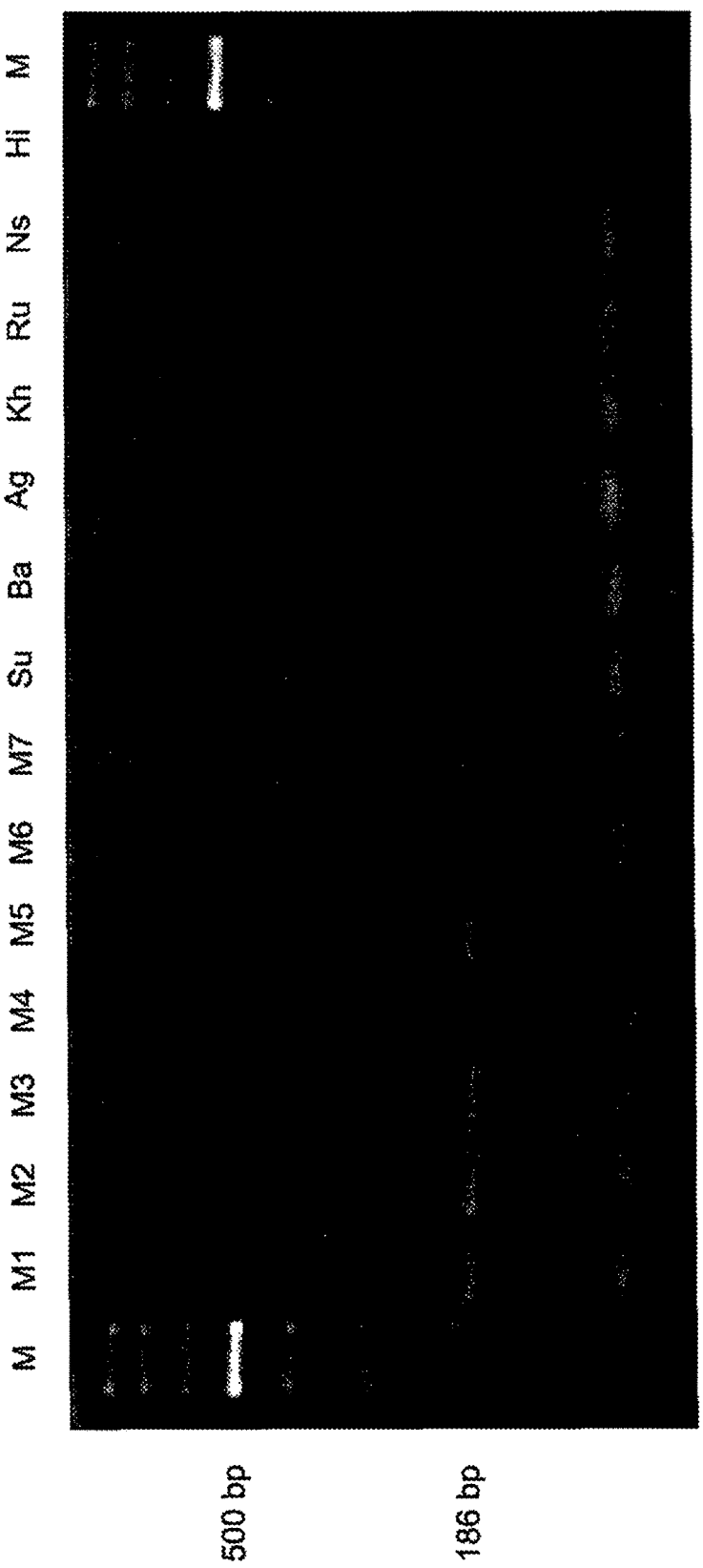
FIG. 2 is an example of the results of gel electrophoresis performed using the Date Palm gender specific SCAR primers (SEQ ID NO: 2 and SEQ ID NO 3) according to the present invention.

One method for contacting under amplification conditions the nucleic acid from the sample with a male-specific Date Palm sex-linked marker primer pair may include subjecting the nucleic acid and the male-specific Date Palm sex-linked marker primer pair to standard polymerase chain reaction ("PCR") cycles. The present inventors were able to determine the sex of different Date Palm plants by conducting PCR screening for the presence of the sex-linked marker in twenty one different Date Palm cultivars, using a male-specific sex-linked marker primer pair. A gel electrophoresis image of PCR amplification products obtained using the oligonucleotide primer including SEQ ID NO: 2 and the oligonucleotide primer including SEQ ID NO: 3 is shown in FIG. 2, where (M) is a 100 base-pair Marker that was used, (M1-M7) are the male cultivars and (Su-Hi) are the female cultivars.

The terms "nucleic acid" and "nucleic acid molecule" may be used interchangeably herein. The terms refer to a deoxyribonucleotide (DNA), ribonucleotide polymer (RNA), RNA/DNA hybrids and polyamide nucleic acids (PNAs) in either single- or double-stranded form, and unless otherwise limited, can encompass known analogs of natural nucleotides that can function in a similar manner as naturally occurring nucleotides.

Nucleic acid extracted from the sample may be isolated using known methods. Nucleic acid can be isolated using, for example, Plant DNAzol Reagent from Life Technologies now Invitrogen (Invitrogen Life Technologies), or DNeasy Mini-Kit (Qiagen). An isolated DNA sequence, for example, is substantially separated or purified away from other nucleic acid sequences with which the nucleic acid is normally associated in the cell of the organism in which the nucleic acid naturally occurs i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids. The term "substantially purified", as used herein, refers to a molecule separated from other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

It should be understood that, in addition to the techniques provided in the Examples herein, any suitable technique for extracting and/or isolating nucleic acids from biological samples that is known in the art may be used to extract nucleic acids and/or isolate nucleic acids from the Date Palm plant sample.

As is known in the art, PCR means a reaction for the in vitro amplification of a specific target nucleic acid sequence and is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. The reaction is cycled through different temperatures optimized for each step in a thermal cycler instrument. Particular temperatures, durations at each step, and rates of change between steps depend on many factors well known to those of ordinary skill in the art.

The term "PCR" further encompasses derivative forms of the reaction, including but not limited to, RT-PCR, real-time PCR, nested PCR, quantitative PCR, multiplexed PCR, and the like. "Reverse transcription PCR" or "RT-PCR" indicates a PCR that is preceded by a reverse transcription reaction that converts a target RNA to a complementary single stranded DNA, which is then amplified. For example, where RNA nucleic acid species may be used for detection of certain nucleotide sequences, a DNA copy (cDNA) of the RNA transcripts of interest can be synthesized prior to the amplification step. The cDNA copy can be synthesized by reverse transcription, which may be carried out as a separate step, or in a homogeneous reverse transcription-polymerase chain reaction, a modification of the polymerase chain reaction for amplifying RNA. "Real-time PCR" means a PCR for which the amount of reaction product, i.e. the amplicon or amplification product, is monitored as the reaction proceeds. There are many forms of real-time PCR that differ mainly in the detection chemistries used for monitoring the reaction product. "Nested PCR" means a two-stage PCR wherein the amplicon of a first PCR becomes the sample for a second PCR using a new set of primers, at least one of which binds to an interior location of the first amplicon. "Multiplexed PCR" means a PCR wherein multiple target sequences (or a single target sequence and one or more reference sequences) are simultaneously carried out in the same reaction mixture.

Any other suitable method for polynucleotide amplification that is well known to one of ordinary skill in the art may be employed. Other amplification methods may include for example, ligase chain reaction ("LCR") and rolling circle amplification ("RCA").

Any well-known methods for detection of amplification products may be employed. In some embodiments, the detection step can comprise gel electrophoresis, capillary electrophoresis, fluorescence resonant energy transfer (FRET), or hybridization to a labeled probe, such as a probe labeled with biotin, a fluorescent moiety, an antigen, a molecular weight tag, radioactive label, or other detectable modification. In some embodiments, the detection step can comprise the incorporation of a label (such as but not limited to fluorescent or radioactive labels) during an extension reaction. The detection step can further comprise measuring fluorescence, mass, charge, and/or chemiluminescence.

Real-time detection of the amplification products may be performed. Real-time detection in the context of amplification indicates an amplification reaction for which the amount of reaction product, i.e. the amplicon or amplification product, is monitored simultaneously with the reaction progression. Amplification products are monitored and quantitated as the amplification products are generated in the reaction mixture. Examples of real-time detection include RT-PCR (real-time polymerase chain reaction) and real-time quantitative PCR).

TaqMan PCR probes may be the basis for detection of the amplification products. TaqMan probes were developed by Applied Biosystems for use with real-time PCR reactions and are commercially available from Applied Biosystems. TaqMan probes comprise an oligonucleotide sequence containing a fluorophore covalently attached to the 5'-end of the oligonucleotide probe and a quencher at the 3'-end. Several different fluorophores (including, 6-carboxyfluorescein (FAM) or tetrachlorofluorescein (TET) and quenchers (e.g., tetramethylrhodamine (TAMRA) or dihydrocyclopyrroloindole tripeptide minor groove binder (MGB)) are available for inclusion in TaqMan probes. The quencher molecule quenches the fluorescence emitted by the fluorophore when excited by an appropriate light source via FRET (Fluorescence Resonance Energy Transfer). Upon extension of the TaqMan probes by Taq polymerase, the 5' to 3' exonuclease activity of the polymerase induces release of the fluorophore and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

In addition to the TagMan fluorescent probes, other fluorescent probes may be used for detection of the amplification products. Fluorophores that may be used for fluorescent probes include but are not limited to DAPI (4',6-dismidino-2-phylindole; FITC (fluorescein isothiocyanate), Dil (1,1'-dihexyl-3,3,3',3'-tetramethlindocarbocyanine perchlorate), BODIPY FL and CY3, as well as any others commonly known to one of skill in the art.

As described above, determining a presence or absence of the Date Palm plant sex-linked marker (SEQ ID NO: 1) in the Date Palm plant sample may include detecting a protein encoded by the Date Palm plant sex-linked marker (SEQ ID NO: 1) using, e.g., an enzyme-linked immunosorbent assay ("ELISA"). The ELISA may be a direct ELISA in which antibodies to the protein encoded by SEQ ID NO: 1 are produced, conjugated with enzymes, and applied directly to the sample prepared for testing. Detection of a binding complex between the protein and the antibody indicates the presence or SEQ ID NO: 1. Preparation of antibodies and the extract from the Date Palm sample for use in the ELISA can be conducted in any suitable manner known in the art.

Also provided are kits for sex determination of a Date Palm plant. A kit for sex determination of a Date Palm plant may include one or more pairs of male-specific sex-linked marker primers and non-specific amplification reagents for amplifying the sex-linked marker. The male-specific sex-linked marker primer pairs May include SEQ ID NO: 2 and SEQ ID NO: 3. The kit may include a nucleic acid probe that binds to an amplified region of the Sex-linked marker. The nucleic acid probe may be fluorescently labeled by any means known to one of ordinary skill in the art.

The kit for sex determination of a Date Palm plant may include an ELISA kit for use in detecting the presence of a protein encoded by SEQ ID NO: 1. The kit may include at least one antibody against the protein encoded by SEQ ID NO: 1 and at least one indicator to detect a binding complex of the protein encoded by SEQ ID NO: 1 and the at least one antibody.

Amplification of the male-specific sex-linked marker (SEQ ID NO: 1) may be performed with the newly designed forward and reverse SCAR primers, ALAMERI-F 5-CGTGGGATGAGGTAGTTTGG-3 (SEQ ID NO: 2) and ALAMERI-R 5-CTCGCGATGCAAACCAACCAA-3 (SEQ ID NO: 3). The newly designed sex-linked marker primers flank a 186-bp region. Amplification may be performed at a high melting temperature, e.g., about 60.5-61.3 degrees Celsius, providing increased specificity.

The following examples are illustrative only, and are not intended to limit the present teachings.

EXAMPLE 1

Extraction of Plant DNA

Genomic DNA was extracted using reagents from Qiagen. Date Palm varieties were collected from Dirab, Saudi Arabia. Small pieces of Date Palm leaf tissue (200 mg) were frozen in liquid nitrogen and ground to a fine powder in a mortar. The frozen-ground tissues were transferred to 2 ml micro-centrifuge tubes and mixed for ten minutes in 800 µl of extraction buffer (preheated to 65 degrees Celsius) with 10 microliters of RNase A (10 mg/ml). Three percent of PVP (Qiagen) and beta-mercaptoethanol were added and mixed by inversion. The mixture was incubated at 65° C. for 30 min, with inversion every five minutes. The mixture was cooled to room temperature, and an equal volume of chloroform: isoamyl alcohol (24:1) was added and mixed frequently for 20 minutes. The mixture was then centrifuged at 10,000 rpm for 10 minutes at room temperature. The aqueous phase was transferred to another tube and an equal volume of ice cooled isopropanol was added. This mixture was incubated at −20 degrees Celsius for 30 minutes. The tubes were centrifuged at 10,000 rpm for 20 minutes and the supernatant was discarded, leaving a pellet of genomic DNA. The pellet was then washed twice with cold 70% ethanol, dried at 37 degrees Celsius, and dissolved in 200 microliters AE buffer (Qiagen).

EXAMPLE 2

RAPD Analysis

Analysis of RAPD was used to screen 300 arbitrary sequence decamer primers (Operon Technologies). Each primer was tested using DNA from seven male and seven female Date Palm cultivars. PCR reactions were performed in 20 microliter reaction volumes containing: 4 microliters 5× HOT FIREPol Blend Master Mix Ready to Load, 2 microliters of the RAPD Primer (15 ng/ul), 2 microliters of the template DNA (25 ng/ul), and 12 microliters of deionized water, DNA amplification was performed using an Applied Biosystems 96 well thermal cycler, with a first cycle of 5 minutes at 94 degrees Celsius, forty cycles of one minute at 94 degrees Celsius followed by one minute at 36 degrees Celsius followed by one minute at 72 degrees Celsius, and one cycle of 7 minutes at 72 degrees Celsius. Amplification products were analyzed by gel electrophoresis in 1.3% agarose gel with 1× TBE (Tris/Borate/EDTA) buffer, Gels were stained with ethidium bromide and visualized with UV light. Each amplification was performed using a single primer and repeated at least three times to verify the results.

EXAMPLE 3

Unique Band Selection From RAPD Profile

A DNA marker that was present in corresponding male or female samples and absent in the alternate sex samples was recognized as a potential sex-linked marker. Further PCR analysis of the corresponding RAPD primer (SEQ ID NO: 4) was performed on additional male and female cultivars to confirm the results.

EXAMPLE 4

Cloning and Sequencing of the Sex-Linked Marker

A candidate sex-linked marker was excised from the gel using the Wizard SV Gel and PCR Clean-Up System from PROMEGA. The candidate sex-linked marker was then sent to MACROGEN, Korea for cloning and sequencing.

EXAMPLE 5

SCAR Primer Design

The ends of the cloned RAPD sex-linked marker sequence (SEQ ID NO 1) were used to design SCAR primers specific to the sex-linked marker (SEQ ID NO: 1). Primer pairs were designed using the publicly available primer 3 tool (http://frodo.wi.mit.edu/) and Primer Select software (DNAStar).

EXAMPLE 6

Testing SCAR Primers

The SCAR primer pairs (SEQ ID NO: 2 and SEQ ID NO: 3) were tested through PCR amplification of seven male and seven female Date Palm cultivars. PCR was performed in 25 microliter reactions, in the presence of: 2 microliters DNA template (25 ng/ul), Illustra PuReTaq Ready-To-Go PCR Beads, 1 microliter Forward Primer (15 ng/ul), 1 microliter Reverse Primer (15 ng/ul), and 20 microliters deionized water, PCR reactions were performed with a first cycle of 4 minutes at 94 degrees Celsius, forty cycles of 30 seconds at 94 degrees Celsius followed by 1 minute at 55 degrees Celsius followed by 30 seconds at 72 degrees Celsius, and one cycle of 7 minutes at 72 degrees Celsius. Amplification products were separated on 1.5% agarose gel (Promega), stained with ethidium bromide, and visualized with UV light.

It is to be understood that the present invention is not limited to the embodiments described above, but encompasses any and all embodiments within the scope of the following claims.

We claim:

1. A sex-determination method for date palm, comprising:
obtaining a sample from a date palm plant; and
determining a presence or absence of the date palm sex-linked marker SEQ ID NO: 1 in the sample,
whereby the presence of the date palm sex-linked marker SEQ ID NO: 1 in the sample is indicative that the sex of the date palm plant is male.

2. The sex-determination method for date palm according to claim 1, wherein the sample includes date palm plant tissue or an extract from the date palm plant issue.

3. The sex-determination method for date palm according to claim 2, wherein the date palm plant tissue is selected from the group consisting of leaves, seeds, petals, flowers, and bark.

4. The sex-determination method for date palm according to claim 1, wherein the sample includes plant body fluid.

5. The sex-detelluination method for date palm according to claim 1, wherein determining a presence or absence of the date palm sex-linked marker SEQ ID NO:1 in the sample includes:
a) extracting nucleic acid from the date palm sample;
b) contacting under amplification conditions the nucleic acid from the sample with a male-specific date palm sex-linked marker primer pair; and
c) detecting the presence or absence of amplification products, whereby the presence of amplification products is indicative of the presence of the date palm sex-linked marker SEQ ID NO: 1 in the sample.

6. The sex-determination method for date palm according to claim 5, further comprising detecting the presence or absence of amplification products having an approximate size of 186 base pairs, whereby the presence of amplification products having an approximate size of 186 base pairs is indicative of the presence of the date palm sex-linked marker SEQ ID NO:1 in the sample.

7. The sex-determination method for date palm according to claim 5, wherein the male-specific sex-linked marker primer pair includes an oligonucleotide including SEQ ID NO: 2 and an oligonucleotide including SEQ ID NO: 3.

8. The sex-determination method for date palm according to claim 5, further comprising isolating the nucleic acid extracted from the sample.

9. The sex-determination method for date palm according to claim 5, wherein the nucleic acid is DNA.

10. The sex-determination method for date palm according to claim 5, wherein the nucleic acid is RNA.

11. The sex-determination method for date palm according to claim 5, wherein the amplification conditions comprise conditions for carrying out polymerase chain reaction (PCR).

12. The sex-determination method for date palm according to claim 1, wherein the presence or absence of the date palm sex-linked marker SEQ ID NO:1 in the sample is determined by detecting a protein in the sample, the protein being a protein that is encoded by the date palm sex-linked marker SEQ ID NO:1, whereby detection of the protein is indicative of the presence of the date palm sex-linked marker SEQ ID NO:1.

13. The sex-determination method for date palm according to claim 12, wherein the protein is detected using an enzyme-linked immunosorbent assay (ELISA).

* * * * *